(12) United States Patent
Losso et al.

(10) Patent No.: US 7,671,242 B2
(45) Date of Patent: Mar. 2, 2010

(54) ISOLATION OF AFLATOXIN-FREE LUTEIN FROM AFLATOXIN-CONTAMINATED PLANTS AND PLANT PRODUCTS

(75) Inventors: Jack N. Losso, Baton Rouge, LA (US); Evdokia Menelaou, Baton Rouge, LA (US); Joan M. King, Baton Rouge, LA (US)

(73) Assignee: Board of Supervisors of Louisiana State University and Agricultural and Mechanical College, Baton Rouge, LA (US)

(*) Notice: Subject to any disclaimer, the term of this patent is extended or adjusted under 35 U.S.C. 154(b) by 987 days.

(21) Appl. No.: 11/315,680

(22) Filed: Dec. 21, 2005

(65) Prior Publication Data

US 2007/0142678 A1 Jun. 21, 2007

(51) Int. Cl.
*C07C 35/21* (2006.01)
*C07C 35/18* (2006.01)
(52) U.S. Cl. .................. 568/816; 568/822; 568/827; 568/832; 568/834
(58) Field of Classification Search ............... 568/816, 568/834, 822, 827, 832
See application file for complete search history.

(56) References Cited

U.S. PATENT DOCUMENTS

| 6,169,217 B1 | 1/2001 | Cheryan ............... 568/816 |
| 6,329,557 B1 | 12/2001 | Rodriguez et al. .......... 568/834 |
| 6,627,797 B1 | 9/2003 | Duvick et al. ............... 800/279 |

FOREIGN PATENT DOCUMENTS

JP 2003-201497 * 7/2003

OTHER PUBLICATIONS

Antony, J.I.X. et al., "Lutein," The World of Food Ingredients, Apr./May, pp. 64-67 (2001).
Menelaou, E., "Isolation of Aflatoxin-Free Lutein from Aflatoxin-Contaminated Corn," A thesis submitted to the Department of Food Science, Louisiana State University, Aug. 2004.
"News: TAMU pilot plant to use acetone as solvent," Inform, vol. 12, pp. 730-731 (Jul. 2001).
Roy, S.K. et al., "Aflatoxin B1 expoxidation catalyzed by partially purified human liver lipoxygenase," Xenobiotica, vol. 27, pp. 231-241 (1997).
Coker, R.D., "The chemical detoxification of aflatoxin-contaminated animal feed," In Natural Toxicants in Food, (ed. D. Watson), Sheffield Academic Press, Kent, England, pp. 284-298 (1998).
Johnson, E.J., "The role of carotenoids in human health," Nutrition in Clinical Care, vol. 5, pp. 56-65 (2002).
Jones, S.T. et al., "Storage stability of lutein during ripening of cheddar cheese," J. Dairy Sci., vol. 88, pp. 1661-1670 (2005).
Li, F.Q. et al., "Aflatoxins and fumonisins in corn from the high-incidence area for human hepatocellular carcinoma in Guangxi, China," J. Agric. Food Chem., vol. 49, pp. 4122-4126 (2001).
Li, H.-B. et al., "Isolation and purification of lutein from the microalga Chlorella vulgaris by extraction after saponification," J. Agric. Food Chem., vol. 50, pp. 1070-1072 (2002).
McLean, M. et al., "Cellular interactions and metabolism of aflatoxin: An update," Pharmac. Ther., vol. 65, pp. 163-192 (1995).
Palanee, T. et al., "Cytotoxicity of aflatoxin B1 and its chemically synthesized epoxide derivative on the A549 human epithelioid lung cell line," Mycopathologia, vol. 151, pp. 155-159 (2000).
Park, D.L., "Perspectives on mycotoxin decontamination procedures," Food Additives and Contaminants, vol. 10, pp. 49-60 (1993).
Piedade, F.S. et al., "Distribution of aflatoxins in corn fractions visually segregated for defects," Brazilian Journal of Microbiology, vol. 33, pp. 250-254 (2002).
Prudente A.D. et al., "Efficacy and safety evaluation of ozonation to degrade aflatoxin in corn," Food Chem. Toxico., vol. 67, pp. 2866-2872 (2002).
Scudamore, K.A., "Mytoxins," in Toxicants in Foods (ed. D. Watson), Sheffield Academic Press, England, pp. 147-174 (1998).
Uraguchi, K. et al., Toxicology: Biochemistry and Pathology of Mycotoxins, Kodansha LTD, Tokyo, Japan, pp. 13-63 (1978).

* cited by examiner

*Primary Examiner*—Elvis O Price
(74) *Attorney, Agent, or Firm*—John H. Runnels; Bonnie J. Davis

(57) ABSTRACT

An efficient method is disclosed for extracting lutein from corn, sweet potato, and other plant products, and for extracting aflatoxin-free lutein from aflatoxin-contaminated plant grains and other plant products safely without any toxic by-products. The lutein is extracted using acetone, and either chilled or saponified to separate from the lipids. If contaminated with aflatoxin, the extracted aflatoxin-contaminated lutein is treated with lipoxidase. This method may be used in producing aflatoxin-free lutein from other contaminated grains or plant oils, or other plant products, including corn, cotton, soybean, rice, barley, wheat, maize, millet, and peanut.

14 Claims, 9 Drawing Sheets

Figure 1:
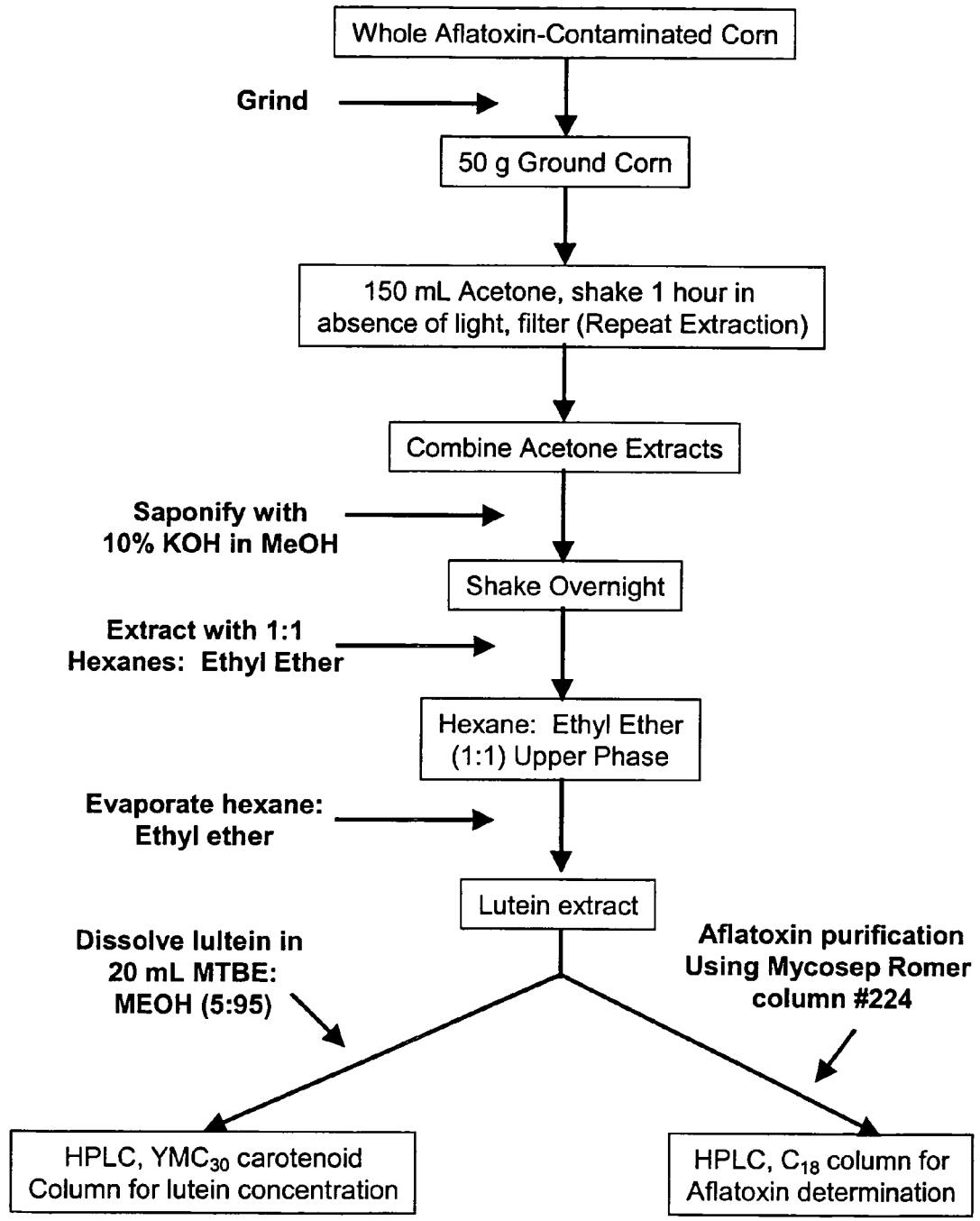

```
Lutein-aflatoxin extract
          │
10 mL Corn Oil ──────▶
          │
          ▼
  Sample in oil + DMSO
          │
2 mg LOX in
0.05 M Tris/HCl ──────▶
(pH 7.2)
          │
          ▼
   Incubate 3 minutes,
   37°C in water bath
          │
Linoleic Acid ──────▶
          │
          ▼
   Incubate 2 hours,
   37°C in water bath
          │
          ▼
Aflatoxin Analysis using MFC$_{224}$
   Mycosep Column Method
```

Fig. 2

ISOLATION OF AFLATOXIN-FREE LUTEIN FROM AFLATOXIN-CONTAMINATED PLANTS AND PLANT PRODUCTS

This invention pertains to a new method using an acetone extraction to isolate lutein from plants, optionally followed by an enzyme treatment to isolate safe, aflatoxin-free lutein from plants or plant products that may be contaminated with aflatoxin (e.g., corn, sweet potato, cotton, peanut, soybean, rice, wheat, millet, maize, and barley).

The fungi, *Aspergillus flavus* and *Aspergillus parasiticus*, that produce aflatoxins before and during harvesting, processing, and storage, can infect important food and feed crops under favorable conditions of temperature (>90° F.) and humidity (>80%). See K. A. Scudamore, "Mycotoxins," in Toxicants in Foods (ed. D. Watson), Sheffield Academic Press, England, pp. 147-174 (1998). *Aspergillus flavus* and *A. parasiticus* are soil-borne fungi that grow on both living and decaying plant tissues.

Corn (*Zea mays*) is a popular and widely consumed food and feed commodity in many communities throughout the world. Corn susceptibility to aflatoxin contamination, however, provides a potential health hazard to both human consumers and animals. See F. S. Piedade et al., "Distribution of aflatoxins in corn fractions visually segregated for defects," Brazilian Journal of Microbiology, vol. 33, pp. 250-254 (2002). Corn is of great importance because of its oil, starch, and protein content. Lutein and zeaxanthin are plant pigments that belong to the group of carotenoids. Because humans are not capable of synthesizing carotenoids in vivo, the presence of lutein in human tissue is solely dependent upon dietary origin. Lutein is found in green leafy vegetables (e.g., kale, spinach, broccoli, green beans) and fruits. In corn, lutein is mostly found in the horny endosperm. Zeaxanthin is a structural isomer of lutein and is similar to lutein relative to food sources, human metabolism, and tissue storage. See E. J. Johnson, "The role of carotenoids in human health," Nutrition in Clinical Care, vol. 5, pp. 56-65 (2002). Both lutein and zeaxanthin are also called xanthophylls or macula pigments.

Lutein

An important characteristic of lutein and zeaxanthin is the presence of nine or more conjugated carbon-carbon double bonds, which allows susceptibility to light, oxygen, heat, and acid degradations. These conjugated double bonds have the ability to quench singlet oxygen with increasing activity depending on the number of conjugated double bonds. This unique structure of lutein and zeaxanthin allows them to function as primary antioxidants in biological systems by scavenging peroxyl radicals. Generally, carotenoids are believed to form resonance stabilized radical cations or radical adducts, which are not capable of participating in autoxidation reactions.

The presence of hydroxyl groups makes lutein and zeaxanthin noticeably more polar than their respective analogs of α- and β-carotene. Lutein is soluble in both nonpolar and polar solvents as shown in Table 1. See J. I. X. Antony et al., "Lutein," The World of Food Ingredients, April/May, pp. 64-67 (2001).

TABLE 1

Lutein: Physical Properties and Solubility in Organic Solvents

A. Physical Properties of Lutein

| | |
|---|---|
| Molecular formula | $C_{40}H_{56}O_2$ |
| Molecular weight | 568.85 |
| Melting point | 183-190° C. |
| Appearance | Yellow prisms with metallic luster |
| Stability | Unstable to light and oxygen; Stable if stored at −20° C. under a nitrogen atmosphere |
| Solubility in water | Insoluble |

TABLE 1-continued

B. Solubility of Lutein in Organic Solvents

| Solvent | Solubility (mg/L) |
|---|---|
| Acetone | 800 |
| Acetonitrile | 100 |
| Benzene | 600 |
| Chloroform | 6000 |
| Cyclohexane | 50 |
| Cyclohexanone | 4000 |
| Dimethyl formamide | 1000 |
| Ethyl alcohol | 300 |
| Ethyl acetate | 800 |
| Ethyl ether | 2000 |
| Hexane | 20 |
| 2-Propanol | 400 |
| Methyl alcohol | 200 |
| Methyl tert butyl ether | 2000 |
| Tetrahydrofuran | 8000 |
| Toluene | 500 |

Adapted from Antony et al., 2001.

Sweet potato leaves are another source of lutein. In foods, lutein can be found either in its free form, bound to proteins, or esterified as a mono- or di-ester. Most lutein and zeaxanthin found in plant leaves are bound to proteins. Lutein and other xanthophylls have been extracted from corn using alcohols, i.e., ethanol and isopropanol, and by extraction after saponification. See U.S. Pat. No. 6,169,217; and H.-B. Li et al., "Isolation and purification of lutein from the microalga *Chlorella vulgaris* by extraction after saponification," J. Agric. Food Chem., vol. 50, pp. 1070-1072 (2002). Although acetone has been proposed as an alternative extraction solvent for cottonseed, it has not been suggested for other plants, and in fact, was found not to be a good extraction solvent for rice bran oil and saw palmetto. See "News: TAMU pilot plant to use acetone as solvent," Inform, vol. 12, pp. 730-731 (July 2001).

Lutein (3,3'-dihydroxy-alpha-carotene) has been identified by the Age-Related Eye Disease Study (AREDS) of the National Institute of Health (NIH) as a dietary compound with the ability to delay the onset or progression of age- and diabetes-related vision loss. Lutein can also be useful in the prevention of other angiogenic diseases such as breast and colon cancer. See U.S. Pat. No. 6,329,557.

Although marigold (*Tagetes erecta*) flowers are an excellent source of lutein, corn (*Zea mays*) has been identified as a more economical source of lutein because more value-added products, such as lutein, oil, and zein (known for its anti-microbial and anti-hypertensive activities), can be isolated from corn than marigold flowers. However, aflatoxin-contaminated corn is banned for use in human foods. New methods are needed to produce aflatoxin-free lutein from aflatoxin-contaminated corn.

Aflatoxins

The term "aflatoxin" usually refers to fungal metabolites produced by *Aspergillus flavus* and *Aspergillus parasiticus* (Scudamore, 1998). These metabolites are named aflatoxin $B_1$ ($AFB_1$), $AFB_2$, $AFG_1$, and $AFG_2$. *Aspergillus flavus* produces two toxins, $AFB_1$ and $AFB_2$; and *Aspergillus parasiti-* cus produces all four toxins ($AFB_1$, $AFB_2$, $AFG_1$, and $AFG_2$). The four compounds are distinguished on the basis of their fluorescence color under long-wave ultraviolet illumination, where B stands for blue and G for green. The subscripts relate to their chromatographic mobility. $AFB_1$ is usually found in the highest concentrations, followed by $AFG_1$, $AFB_2$, and $AFG_2$ (McLean et al., 1995). Aflatoxin $M_1$ ($AFM_1$) and aflatoxin $M_2$ ($AFM_2$) are hydroxylated forms of $AFB_1$ and $AFB_2$. Aflatoxin $B_{2a}$ ($AFB_{2a}$) and aflatoxin $G_2a$ ($AFG_{2a}$) are 8,9-hydrated products of $AFB_1$ and $AFG_1$, respectively. These compounds are not as toxic as $AFB_1$ and $AFG_1$.

Aflatoxins are highly soluble in moderately polar solvents (e.g., chloroform and methanol), and have some water solubility. Aflatoxin $B_1$, the most potent of these mycotoxins, is usually found in the highest concentration and causes primary liver cancer. See M. McLean et al., "Cellular interactions and metabolism of aflatoxin: An update," Pharmac. Ther., vol. 65, pp. 163-92 (1995). $AFB_1$ is both lipid and water soluble. These characteristics assist its accumulation and passage through cell membranes and into cellular organelles. Aflatoxins are heat stable and undergo partial or no destruction under ordinary cooking conditions or during pasteurization. $AFB_1$ decomposes without melting at 268-269° C. From a toxicological point of view, aflatoxin can act as a potent toxin, a mutagen, a teratogen, and a carcinogen. According to epidemiological studies, there is evidence relating $AFB_1$ to primary liver cancer. See F. Q. Li et al., "Aflatoxins and fumonisins in corn from the high-incidence area for human hepatocellular carcinoma in Guangxi, China," J. Agric. Food Chem., vol. 49, pp. 4122-4126 (2001). Aflatoxin itself is not directly carcinogenic; but when ingested, it can be metabolized by the body to produce an ultimate carcinogenic metabolite known as $AFB_1$-8,9-epoxide. The biotransformation to the epoxide is accomplished by a bioactivation system and subsequent covalent binding to DNA or proteins. See T. Palanee et al., "Cytotoxicity of aflatoxin $B_1$ and its chemically synthesized epoxide derivative on the A549 human epithelioid lung cell line," Mycopathologia, vol. 151, pp. 155-159 (2000); and S. K. Roy et al., "Aflatoxin $B_1$ expoxidation catalyzed by partially purified human liver lipoxygenase," Xenobiotica, vol. 27, pp. 231-241 (1997).

Aflatoxin-producing fungi require appropriate conditions to produce aflatoxin as a secondary metabolite. Production is favored by certain environmental conditions, such as temperature (>90° F.), humidity (>80%), the oxygen level, and chemical characteristics of the agricultural products that serve as the substrate for aflatoxin production. Additionally, improper storage conditions allow spores to develop and subsequently produce aflatoxins. Contamination throughout a load of feed is often not uniform, which makes effective sampling very difficult.

One of the main reasons aflatoxins are widely distributed is that *A. flavus* is naturally found in air and soil worldwide. *Aspergillus flavus* deteriorates a number of stored crops, such as corn, cottonseed (*Gossypium herbaceum*), rice (*Oryza sativa*), barley (*Hordeum vulgare*), peanuts (*Arachis hypogaea*), wheat (*Triticum aestivum*), and millet. See K. Uraguchi et al., Toxicology: Biochemistry and Pathology of Mycotoxins, Kodansha LTD, Tokyo, Japan, pp. 288 (1978). During storage, this toxic mold grows at relatively low moisture levels. Aflatoxins are more common in grains from southern regions and are rare in northern areas of the USA. However, severe drought conditions during grain fill can favor aflatoxin contamination of corn crops, creating concerns for marketing and utilizing corn. Furthermore, contamination may also occur when agricultural commodities are not promptly dried or properly stored.

Although aflatoxin $B_1$ is a ubiquitous contaminant of several agricultural crops, contamination of corn likely poses the greatest health risk to humans worldwide, due primarily to the importance of this commodity as a food and feed source throughout the world. Direct economic losses result from the presence of aflatoxin in agricultural crops, including reduced crop quality, crop yield, animal performance and reproduction capabilities, and increased incidence of diseases.

Aflatoxin contamination is a worldwide unavoidable problem. Several strategies have been tried for the detoxification or decontamination of commodities containing mycotoxins. These strategies can be classified as chemical, microbiological, or physical. Many studies have evaluated the use of chemicals for the detoxification and decontamination of contaminated raw materials by destroying or modifying mycotoxins to reduce or eliminate toxic effects. Often chemical treatments have been used in combination with physical treatments to increase the efficacy of decontamination. A variety of chemicals (e.g., acids, bases, aldehydes, bisulfite, oxidizing agents, and various gases) can destroy or degrade aflatoxins effectively, but most are impractical or potentially unsafe to use because of the formation of toxic residues or the effect on nutrient content, flavor, odor, color, texture, and functional properties of the resulting product.

Ammoniation is commonly used for detoxification of aflatoxins. The ammoniation process, using either ammonium hydroxide or gaseous ammonia, has been shown to reduce aflatoxins (100-4000 mg/kg) by up to 99% in corn, peanut meal-cakes, whole cottonseed, and cottonseed products. If the reaction is allowed to proceed to completion, the process is irreversible. See D. L. Park, "Perspectives on mycotoxin decontamination procedures," Food Additives and Contaminants, vol. 10, pp. 49-60 (1993). A high pressure/high temperature ammoniation process (80-120° C./35-50 psi) for 20-60 minutes is used to remove aflatoxin from cottonseed and from cottonseed meal. The efficacy of ammoniation treatment to significantly reduce the toxicity (hepatic neoplasia, immunotoxicity) of aflatoxins has been demonstrated by feeding animals both ammonia-treated and untreated aflatoxin-contaminated corn, peanut meal and mixed feed. Some states permit the ammoniation of cottonseed and corn feed products. However, these products are not approved for human consumption due to the production of at least some toxic products from the ammoniation. See R. D. Coker, "The chemical detoxification of aflatoxin-contaminated animal feed," In Natural Toxicants in Food, (ed. D. Watson), Sheffield Academic Press, Kent, England, pp. 284-298 (1998):

A second method to detoxify aflatoxin-contaminated plant: material is by ozonation. Ozone is a powerful oxidant, which can react with many different compounds. Contaminated corn is treated with ozone gas for a given period of time to reduce the mutagenic potential of aflatoxin-contaminated corn. A. D. Prudente et al., "Efficacy and safety evaluation of ozonation to degrade aflatoxin in corn," J. Food Science, vol. 67, pp. 2866-2872 (2002). Although significantly reducing the amount, ozonation does not completely eliminate the presence of aflatoxin.

U.S. Pat. No. 6,627,797 describes a lipoxygenase isolated from corn, and a method to alter the in vivo concentration of lipoxygenase in plants to reduce the level of aflatoxin contamination in vivo.

There exists a need for a process to completely remove the aflatoxin from contaminated grain products without producing toxic by-products.

We have discovered a new, efficient method for extracting lutein from harvested corn or other plant products using acetone, and a new method to extract aflatoxin-free lutein from aflatoxin-contaminated plant grains and other harvested plant products. Aflatoxin-contaminated lutein was extracted from aflatoxin-contaminated corn using acetone, and subsequently treated with lipoxidase to isolate the aflatoxin product. Chromatographic analysis confirmed that lutein was present, and that aflatoxin was completely removed by the enzymatic treatment, and that no toxic by-products had been produced. The mean aflatoxin-contaminated lutein concentration prior to lipoxidase treatment was 1.10 mg/100 g (dry wt.). Following lipoxidase treatment and extraction with hexane: ethyl ether, the aflatoxin-free lutein recovered was approximately 0.97 mg/100 g (dry wt.), a recovery of 88%. This method can also be used to produce aflatoxin-free lutein from other grains, plant oils, or other plant products that may be contaminated with aflatoxin, e.g., cotton, sweet potato, peanut, soybean, rice, barley, wheat, millet, and peanut.

BRIEF DESCRIPTION OF DRAWINGS

FIG. 1 is a flow diagram illustrating one embodiment of a method to extract lutein from corn kernels.

FIG. 2 is a flow diagram illustrating one embodiment of a method to remove aflatoxin from aflatoxin-contaminated lutein.

FIG. 3 illustrates a HPLC (high performance liquid chromatography) chromatogram showing the elution profile of 50 ppm lutein, under HPLC conditions optimized to detect lutein.

FIG. 4 illustrates a HPLC chromatogram showing the elution profile of lutein isolated from aflatoxin-contaminated corn, under HPLC conditions optimized to detect lutein.

FIG. 5 illustrates a HPLC chromatogram showing the elution profile of 100 ppb aflatoxin, under HPLC conditions optimized to detect aflatoxin.

FIG. 6 illustrates a HPLC chromatogram showing the elution profile of aflatoxin-contaminated corn, under HPLC conditions optimized to detect aflatoxin.

FIG. 7 illustrates a HPLC chromatogram showing the elution profile of an enzyme-treated lutein extract from aflatoxin-contaminated corn, under HPLC conditions optimized to detect aflatoxin.

FIG. 8 illustrates a HPLC chromatogram showing the elution profile of lutein for an enzyme-treated lutein extract from aflatoxin-contaminated corn, under HPLC conditions optimized to detect lutein.

FIG. 9 illustrates a HPLC chromatogram showing the elution profile of lutein for an enzyme-treated lutein extract from aflatoxin-contaminated corn, after spiking with 12.5 ppm lutein, under HPLC conditions optimized to detect lutein.

The available methods for the detoxification of aflatoxin-contaminated corn currently involve the use of ammoniation or ozonation. Both methods generate toxic compounds, and destroy the oil and protein in corn. More importantly, the decontaminated corn product produced by ammoniation or ozonation is not approved for use in human food. The instant invention generates aflatoxin-free lutein and aflatoxin-free corn oil from a contaminated corn oil sample. The method involves lutein extraction with acetone, followed by the isolation of corn oil using traditional solvents such as hexane, and the removal of zein using isopropanol. Using acetone is advantageous in that acetone breaks the bonds between lutein and protein better than ethanol or other organic solvents. Moreover, solubility of lutein in acetone is better than in ethanol. The isolated lutein is extracted along with aflatoxin while a minimal amount of aflatoxin is left behind with the corn oil and proteins, as proven by high performance liquid chromatography. (Data not shown) The lutein-aflatoxin fraction is then treated with a soy enzyme, lipoxidase, to epoxidize aflatoxin. The epoxidized aflatoxin will separate into an aqueous phase, while the aflatoxin-free lutein will stay in the organic phase. This method was shown to be efficient in extracting aflatoxin-free lutein from aflatoxin-contaminated corn. This method will also remove aflatoxin from other potential plant sources, e.g., cotton, rice, barley, peanut, soybean, etc.

Lutein from aflatoxin-contaminated corn was isolated using commercially available solvents. Aflatoxins in the aflatoxin-lutein mixture were enzymatically converted into water-soluble molecules using lipoxidase and were extracted from the lipid phase. Extraction and quantification of aflatoxin in the aqueous and lutein-containing lipid phase were carried out using a multifunctional column method involving solid phase extraction and HPLC, respectively. Aflatoxins $B_1$ and $B_2$ were identified at 4888 and 368 ppb, respectively in the untreated aflatoxins-lutein extract. However, following the enzyme treatment, no peaks associated with either aflatoxin $B_1$ or $B_2$ were detected in the lipid phase-containing lutein. Lutein concentration and stability following enzymatic treatment was determined by HPLC. The HPLC results indicated the presence of one peak eluting at 21.0 minutes. Spiking with standard lutein confirmed the identity and stability of lutein isolated from aflatoxins-contaminated corn.

EXAMPLE 1

Materials and Methods

Materials

Lutein standard, linoleic acid, and lipoxidase were purchased from Sigma Chemical Co. (St. Louis, Mo.). The lipoxidase was used to catalyze the oxidation of an unsaturated fatty acid by atmospheric dioxygen, e.g., soybean (*Glycine max*) lipoxidase (also, called lipoxygenase). The HPLC column ($YMC_{30}$) was purchased from Waters Corp. (Milford, Mass.). Whole corn samples with varying concentrations of aflatoxins were provided by Louisiana Agricultural Experiment Station and the Department of Agronomy, Louisiana State University (Baton Rouge, La.). All reagents were either HPLC grade or reagent grade. Corn oil was purchased from a local grocery store and used without any further purification. The Multifunctional Cleanup system (MFC) (Mycosep Romer column #224) was obtained from Romer Laboratories, Inc. (Washington, Mo.).

Corn Sample Preparation

Whole ears of aflatoxin-contaminated corn were used for a preliminary analysis. Twenty varieties of aflatoxin-contaminated corn samples (200 g each) (Table 1) were used for evaluation of the protocol. Aflatoxin-contaminated corn kernels (200 g) were ground using a Brinkman mill (Brinkman Instruments; Westbury, N.Y.) and passed through a No. 20 mesh screen. Samples were then transferred into clean plastic bags, labeled, and stored at room temperature for 24 hr until analysis.

TABLE 2

Lutein Concentration Of Aflatoxin-Contaminated Corn Samples

| Sample | Lutein concentration (mg/100 g corn) (mean ± S.D.) |
|---|---|
| AR16026: N12 | 1.20 ± 0.03 |
| UR10001: S1813 | 1.07 ± 0.03 |
| PRICGP3: N1211c | 1.11 ± 0.005 |
| ANTIG03: N12 | 1.13 ± 0.07 |

TABLE 2-continued

Lutein Concentration Of Aflatoxin-Contaminated Corn Samples

| Sample | Lutein concentration (mg/100 g corn) (mean ± S.D.) |
|---|---|
| CH05015: N12 | 1.13 ± 0.04 |
| UR10001: S18 | 1.19 ± 0.09 |
| BR52051: S17 | 1.18 ± 0.01 |
| CH05015: N15 | 1.09 ± 0.05 |
| AR16035: S02 | 1.04 ± 0.005 |
| BR51675: N0620 | 1.08 ± 0.045 |
| AR13026: S15 | 1.10 ± 0.03 |
| ANTIG01: N16 | 1.15 ± 0.06 |
| PRICGP3: N1218 | 1.02 ± 0.00 |
| DKB844: N11b | 1.16 ± 0.02 |
| CHIS775: N1920 | 1.05 ± 0.01 |
| GT-mas: gk | 1.12 ± 0.02 |
| CHIS775: S1911b-327-1-B | 1.13 ± 0.02 |
| FS8B(T): N1802-45-1-1SIB-B-B | 1.03 ± 0.01 |
| UR13085: N0215-14-1-B | 1.10 ± 0.04 |
| CHIS775: S1911b-327-1-B | 1.05 ± 0.01 |

Lutein Extraction

Aflatoxin-contaminated ground corn samples (50 g) were treated with acetone using a 1:3 corn:solvent ratio. The mixture was shaken for 1 hr in the absence of light to inhibit lutein decomposition, and then filtered using Whatman No. 4 filter paper. The filtrate was saved, and the extraction process repeated. The filtrate (combination of both extractions) was then evaporated using a Buchi Rotavapor R-200 evaporator (Brinkman Instruments Inc., Westbury, N.Y.). Saponification was achieved by dissolving the extract in 10% potassium hydroxide in methanol. The samples were shaken overnight in the dark. To extract lutein, the sample was combined with hexane:ethyl ether (1:1) in a separatory funnel. The lutein dissolved in the hexane:ethyl ether solution. The lower aqueous phase was washed with the hexane/ethyl ether solution for re-extraction until the aqueous phase was colorless. All hexane: ethyl ether extracts, which contained the lutein, were combined and evaporated. The evaporated extracts were dissolved in 20 mL of methanol: methyl-tert-butyl-ether (MTBE) (95:5 dilution), and the solution passed through a 0.4 μm TFE filter membrane (Millipore, Bedford, Mass.) for HPLC analysis or stored at −20° C. until use. FIG. 1 illustrates this extraction procedure.

To use the lutein as a food additive, the evaporated extract from the hexane:ether extraction was dissolved in ethanol and the solvent removed under vacuum. These two steps were repeated at least three times to remove traces of the hexane: ether mixture. The recovered lutein was stored at −20° C. until use.

HPLC Determination of Lutein from Corn Extracts

To develop a standard curve, lutein standards were prepared in parts per million (ppm) concentrations. Lutein standard (dried powder) was dissolved to the desired concentration using the mobile phase solvent, MTBE:MeOH (5:95). Three milliliters of the corn pigment extract as described above, or of the lutein standards, were filtered through a 0.2 μm TFE filter membrane. The filtered samples were injected into an $YMC_{30}$ carotenoid 3 g, 4.6×250 mm HPLC column. The HPLC separation was conducted using a Waters Model 600E solvent delivery system fitted with a model 717A plus autosampler, a Model 486 tunable absorbance detector, and Millennium 32 chromatography manager processor (Waters Corp.; Milford, Mass.). The flow rate was 1 ml/min, detection was set at 450 nm, the injection volume was 20 μl, and separation was isocratic using MTBE:methanol (5:95) as the mobile phase. The total separation time was 30 min.

Peaks on the HPLC chromatograph were identified by comparing the retention times and spectra with those of the lutein standards. A calibration curve was constructed by plotting the area under the peak against lutein concentration between 0 and 100 ppm. Lutein concentration in corn samples was determined by using a regression equation obtained from the calibration curve.

Enzymatic Treatment of Extracted Lutein Residue

Extracted samples with approximately 0.55 mg lutein (from the procedure described above) were dissolved in approximately 10 mL of corn oil for. further treatment with lipoxidase (LOX). The incubation mixture contained 1.0 mL Tris-HCl, 50 μg lipoxidase, and 50 μm $AFB_1$ in 20 μL DMSO. Buffers at several pH values from about pH 7.0 to about pH. 8.0 were tried. The pH values that resulted in the most efficient removal of aflatoxin from the lutein were values from about pH 7.0 to pH 7.4, with the best value about pH 7.2. A sample extract dissolved in corn oil and the incubation DMSO solution were combined in a 1:1 ratio. After pre-incubation for 3 min at 37° C., the reaction was initiated by the addition of the desired polyunsaturated fatty acid, e.g., linoleic acid, and incubated at 37° C. for a time between about 2 hr and about 18 hr. FIG. 2 illustrates the above procedure. When the enzyme treatment was complete, the samples were divided into two aliquots. One aliquot was used to test for aflatoxin using a Mycosep Romer column #224 as described below. The other aliquot was saponified, lutein was extracted, and analyzed by HPLC as described above. Samples were stored at −20° C. before HPLC analysis for aflatoxin determination.

Aflatoxin Purification

The samples were analyzed following the approved Multifunctional Column (Mycosep) method of the Association of Official Analytical Chemists (AOAC), as described in AOAC, "Official Methods of Analysis," $17^{th}$ ed., Arlington, Va., AOAC International (2000). The treatment protocol included a set of control corn samples, both clean and aflatoxin-contaminated corn. Fifty grams of clean ground corn were mixed with 100 ml of an acetonitrile:water (9:1) solution. The samples were placed on a shaker in the absence of light for 30 min, and then filtered using Whatman No. 4 filter paper. The same procedure was performed with the treated and untreated aflatoxin-contaminated corn. Control samples and treated samples were purified through the Multifunctional cleanup column (Romer Labs, Inc.; Union, Mo.). Approximately 2 ml of the samples were placed in a culture tube, and the flanged-end of the column was pushed into the extract, letting extract pass through the column. An aliquot of the purified extract was used for quantification of aflatoxins as described below.

Quantification of Aflatoxins by High Performance Liquid Chromatography

The samples were analyzed according to the AOAC-approved Multifunctional Column (Mycosep) Column (AOAC Official Method 994.08, 2000). Initially, aflatoxins were derivatized by adding a 200 μl aliquot of the purified extracts into an HPLC auto-injector vial (Waters Corp.; Milford, Mass.), and 700 μl of trifluoroacetic acid derivatizing reagent [distilled water:trifluoroacetic acid:glacial acetic acid (7:2:1)]. The samples were placed in a water bath at 65° C. for 8.5 min. The vials were cooled in an ice-water bath. The samples were placed in the HPLC autosampler (Waters 717). The injection volume was 50 μl, and the total separation time was 15 min. Aflatoxin levels were determined using a Waters 510 HPLC (Waters Corp.; Milford, Mass.) equipped with a Waters 470 fluorescence detector (360 nm excitation and 440 nm emission), and a NovaPak $C_{18}$ reverse phase column (Waters, 3.9 mm×150:mm) using water: acetonitrile (8:2 v/v) as a mobile phase with a flow rate of 2 ml/min. The approximate retention times for aflatoxin $G_1$, $B_1$, $G_2$, and $B_2$ were 2.2, 3, 5.5, and 8.3 min, respectively. Aflatoxin concentrations were calculated by using a plotted standard curve generated by the Millennium Chromatograph Manager Software (Waters Corp.; Milford, Mass.).

Evaluation of Lutein Stability by High Performance Liquid Chromatography

Following the LOX enzymatic treatment of the lutein residue, the lutein samples were extracted using hexane: ethyl ether (1:1). Following extraction, the solvent was evaporated using a Buchi Rotavapor R-200 evaporator (Brinkman Instruments Inc., Westbury, N.Y.). The isolated lutein extract was dissolved in MTBE:MeOH (5:95) for HPLC analysis as described above to determine the presence of lutein and the absence of aflatoxin.

EXAMPLE 2

Identification of Lutein in Aflatoxin-Contaminated Corn

Figure 3:
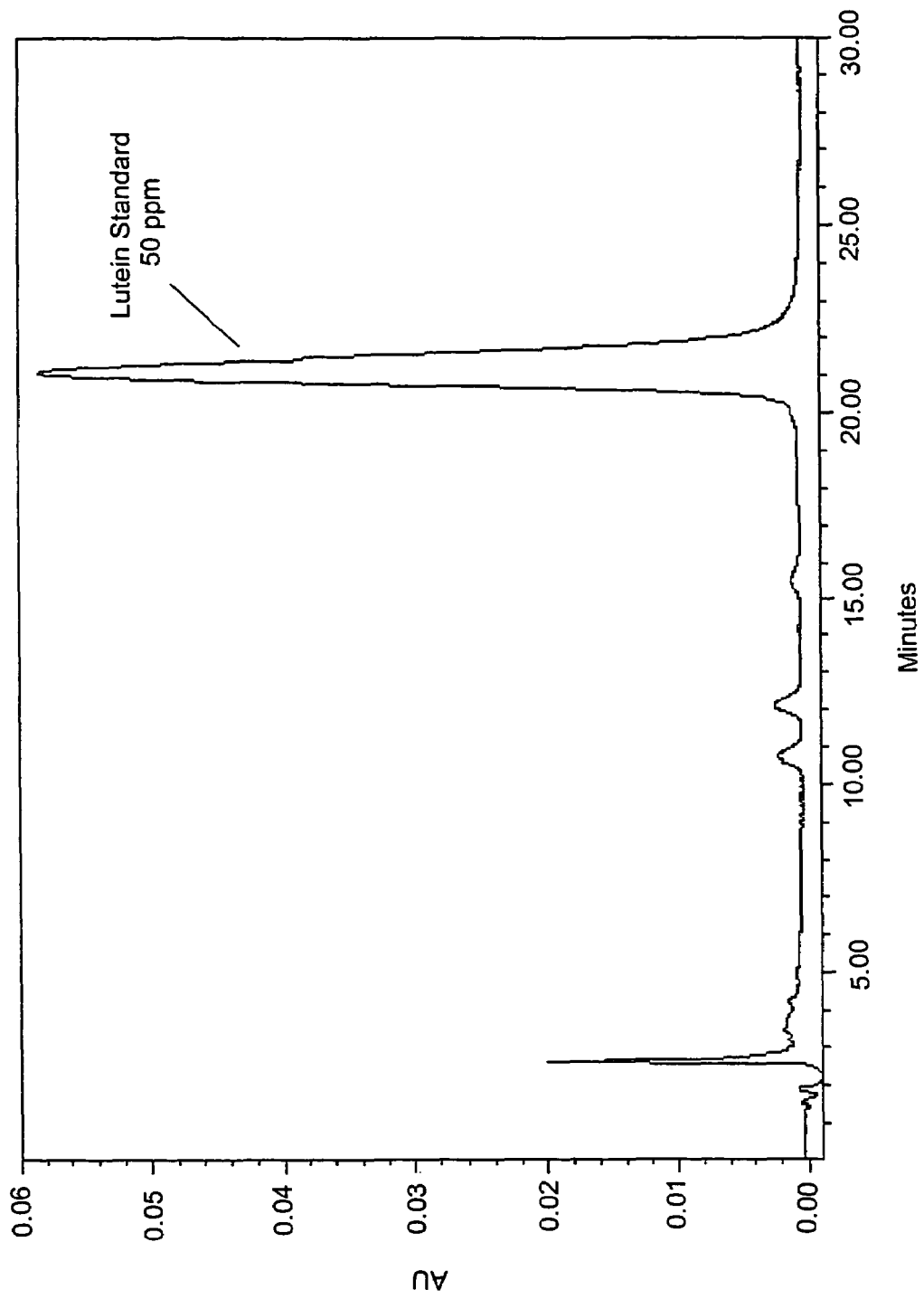

The elution time of the lutein standard using the $YMC_{30}$ carotenoid column and reverse-phase chromatography was less than 30 min. An elution profile for lutein (50 ppm) is shown in FIG. 3. To obtain satisfactory lutein separation in the column, lutein should be completely extracted and released from its ester form. In this analysis, this was accomplished by saponification, which also eliminated contaminating substances such as lipids and proteins that could potentially plug the carotenoid column. See E. E. Moros et al., "Analysis of xanthophylls in corn by HPLC," J. Agric. Food Chem., vol. 50, pp. 5787-5790 (2002).

As shown in FIG. 3, a peak for lutein was distinguished using HPLC and the $C_{30}$ column. Lutein standards of varying concentrations from 25 to 100 ppm were eluted and separated for standard curve determination. A calibration curve was drawn for lutein concentration versus peak area. The content of lutein in the samples was then calculated using peak area to find concentration. Aflatoxin-contaminated corn samples were analyzed for lutein by HPLC.

Figure 4:
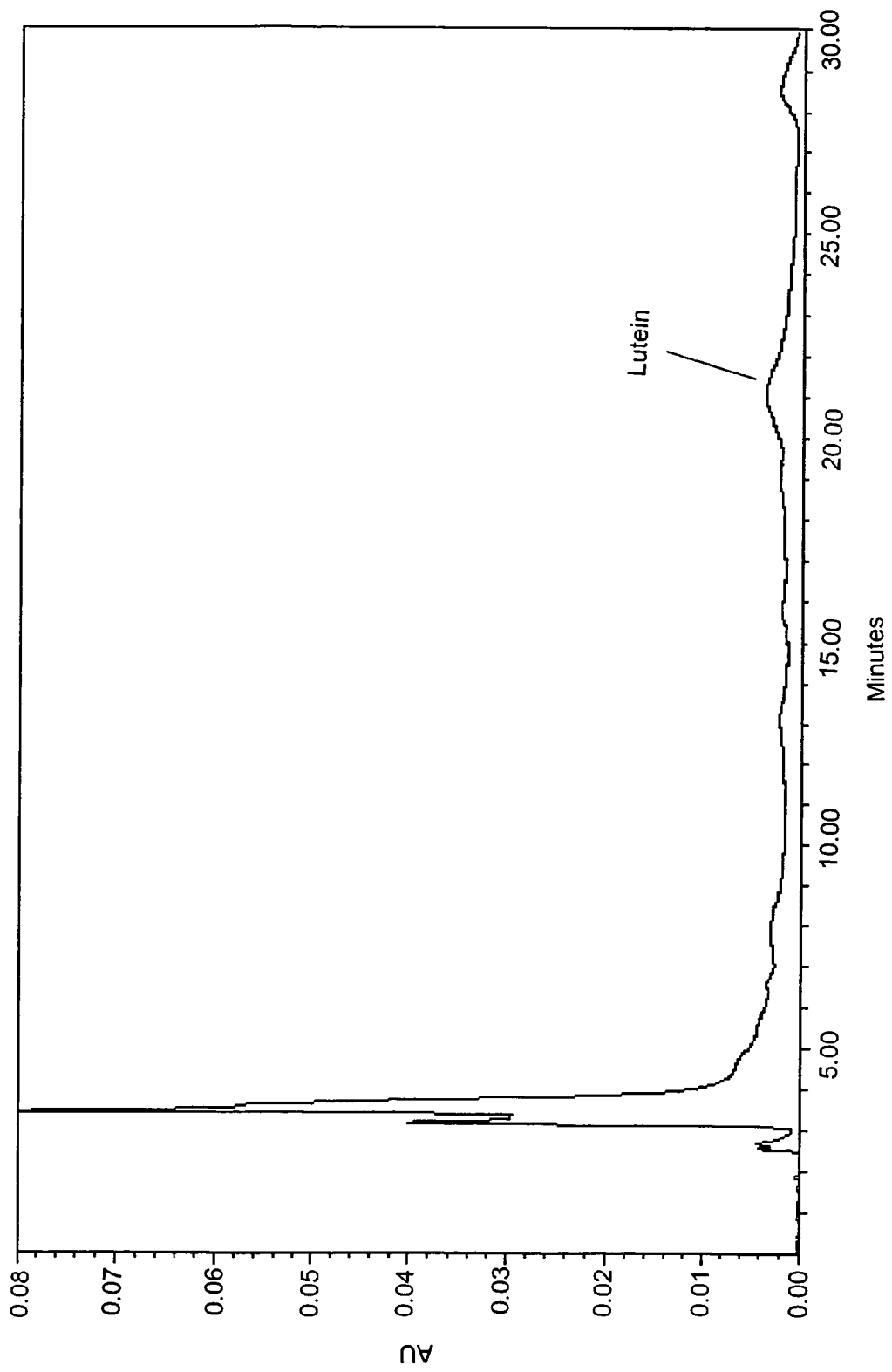

The chromatogram in FIG. 4 illustrates the elution of lutein from aflatoxin-contaminated corn with a retention time similar to the lutein standard shown in FIG. 3, i.e., approximately 21 min. Approximately 1.61 mg of lutein was extracted from 100 g of aflatoxin-free corn, and approximately 1.10 mg of lutein from 100 g of aflatoxin-contaminated corn samples (Table 3). The amount of lutein recovered appeared somewhat decreased in the aflatoxin-contaminated corn.

TABLE 3

Lutein Concentrations from HPLC Analysis.

| Sample | Lutein concentration (mg/100 g corn)* |
|---|---|
| Aflatoxin-free corn | 1.61 ± 0.06 |
| Aflatoxin-contaminated lutein extract | 1.10 ± 0.07 |
| Enzyme-treated lutein extract | 0.97 ± 0.04 |

*Values are mean concentrations ± SD.

Repetitive analysis of 20 varieties of aflatoxin-contaminated corn samples using HPLC demonstrated approximately uniform lutein content (Data not shown). The mean concentration of lutein from the samples analyzed by HPLC before the lipoxidase treatment was 1.10 mg/100 g (dry wt.) of aflatoxin-contaminated corn, with a standard deviation of 0.07 (Table 3).

EXAMPLE 3

Figure 5:
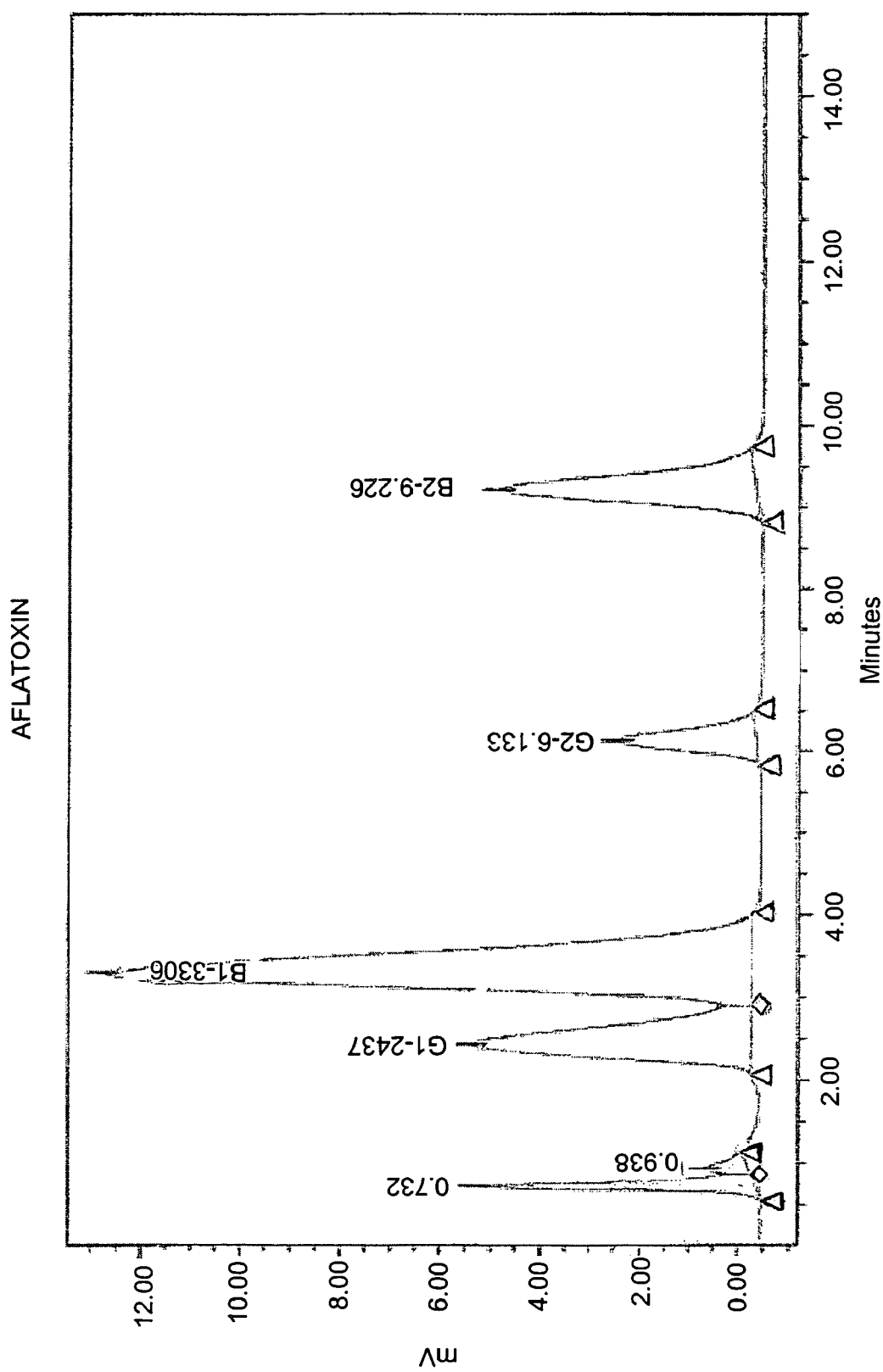

Enzymatic Treatment of Aflatoxin-Contaminated Corn and Determination of Aflatoxins Aflatoxin levels were determined by analyzing the samples following the Multifunctional Column (Mycosep) method as described by A. D. Prudente Jr. et al., "Efficacy and safety evaluation of ozonation to degrade aflatoxin in corn," J. Food Science, vol. 67, pp. 2866-2872 (2002). The samples were enzymatically treated and analyzed with HPLC following the cleanup procedure as described above in Example 1. FIG. 5 represents the elution profile of a mixture of aflatoxin standards, each with a concentration of 100 ppb. Four peaks were identified with $AFG_1$ eluting first, followed by $AFB_1$, $AFG_2$, and lastly $AFB_2$. Approximate retention times for $AFG_1$, $AFB_1$, $AFG_2$, and $AFB_2$ were 2.4, 3.3, 6, and 9.2 min, respectively (FIG. 5). Aflatoxin-free corn was also analyzed under the same conditions, and no aflatoxin peaks were identified. (Data not shown) This indicated that aflatoxin was either not present or present at very low, non-detectable levels.

Figure 6:
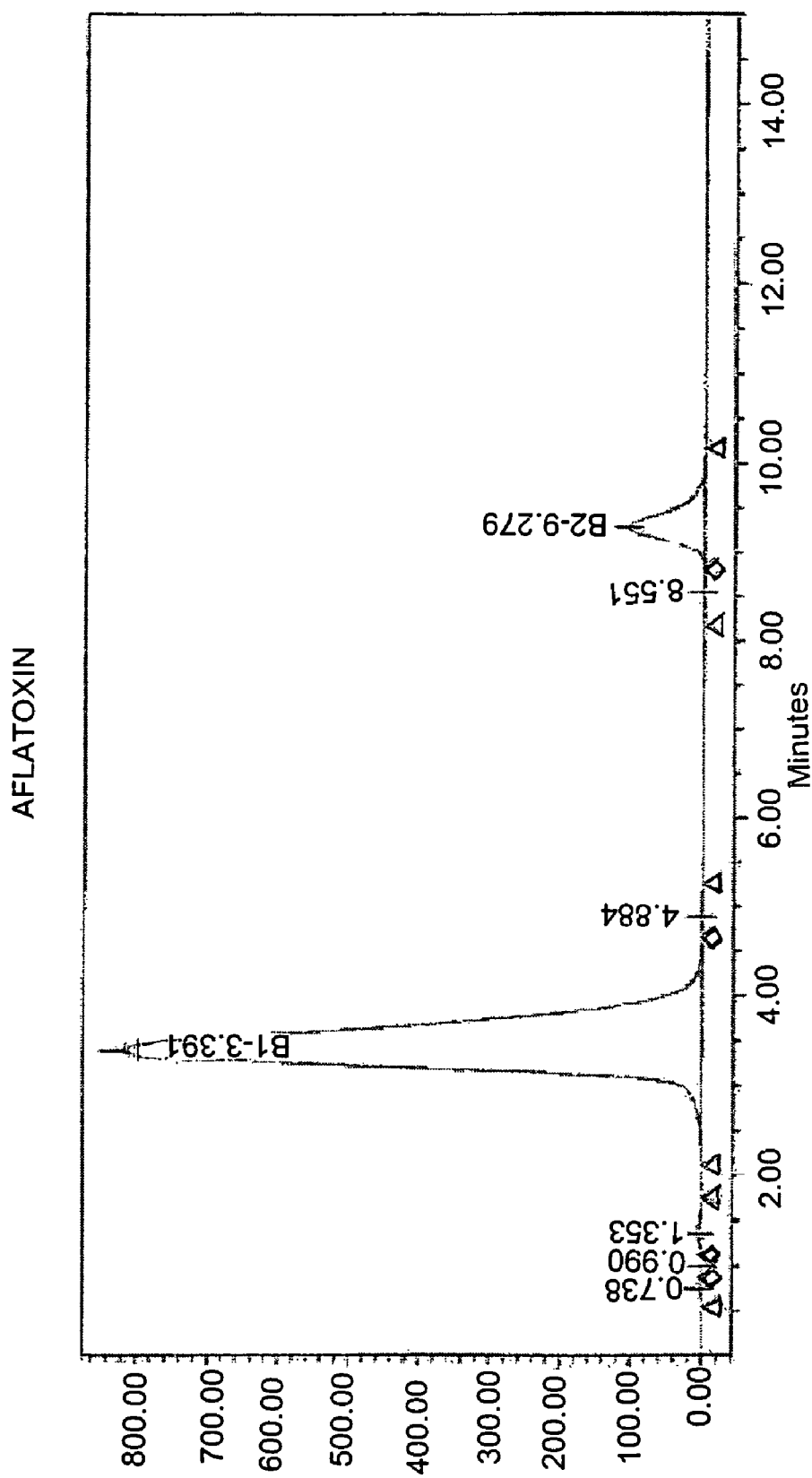

A representative aflatoxin-contaminated corn sample was extracted with acetonitrile:water (9:1) and analyzed for aflatoxin via HPLC. The HPLC profile of this sample is shown in FIG. 6. Two peaks were identified that were associated with $AFB_1$ and $AFB_2$, respectively. No peaks were identified for $AFG_1$ and $AFG_2$. The retention times of $AFB_1$ and $AFB_2$ were 3.4 and 9.3 min, respectively. A similar representative sample of aflatoxin-contaminated corn was extracted for lutein using acetone, saponification, hexane:ethyl ether extraction, evaporation, dissolution in acetonitrile:water (9:1), mycosep column purification of aflatoxin followed by HPLC analysis of aflatoxins. Chromatographic analysis of aflatoxin-contaminated lutein extract also showed peaks of $AFB_1$ and $AFB_2$ at retention times of 3.4 and 9.1 min, respectively (Data not shown).

Aflatoxin concentrations were calculated using the Millennium Chromatography: Manager Software (Waters Corp., Milford, Mass.) (Table 4). The analyzes of aflatoxin concentrations demonstrated that the aflatoxin forms present in higher amounts were $AFB_1$ and $AFB_2$ (Table 4). Based on the results of the aflatoxin concentrations as measured by HPLC, the LOX enzyme treatment eliminated the aflatoxin present in corn, or at least reduced it to non-detectable levels (FIG. 7).

Figure 7:
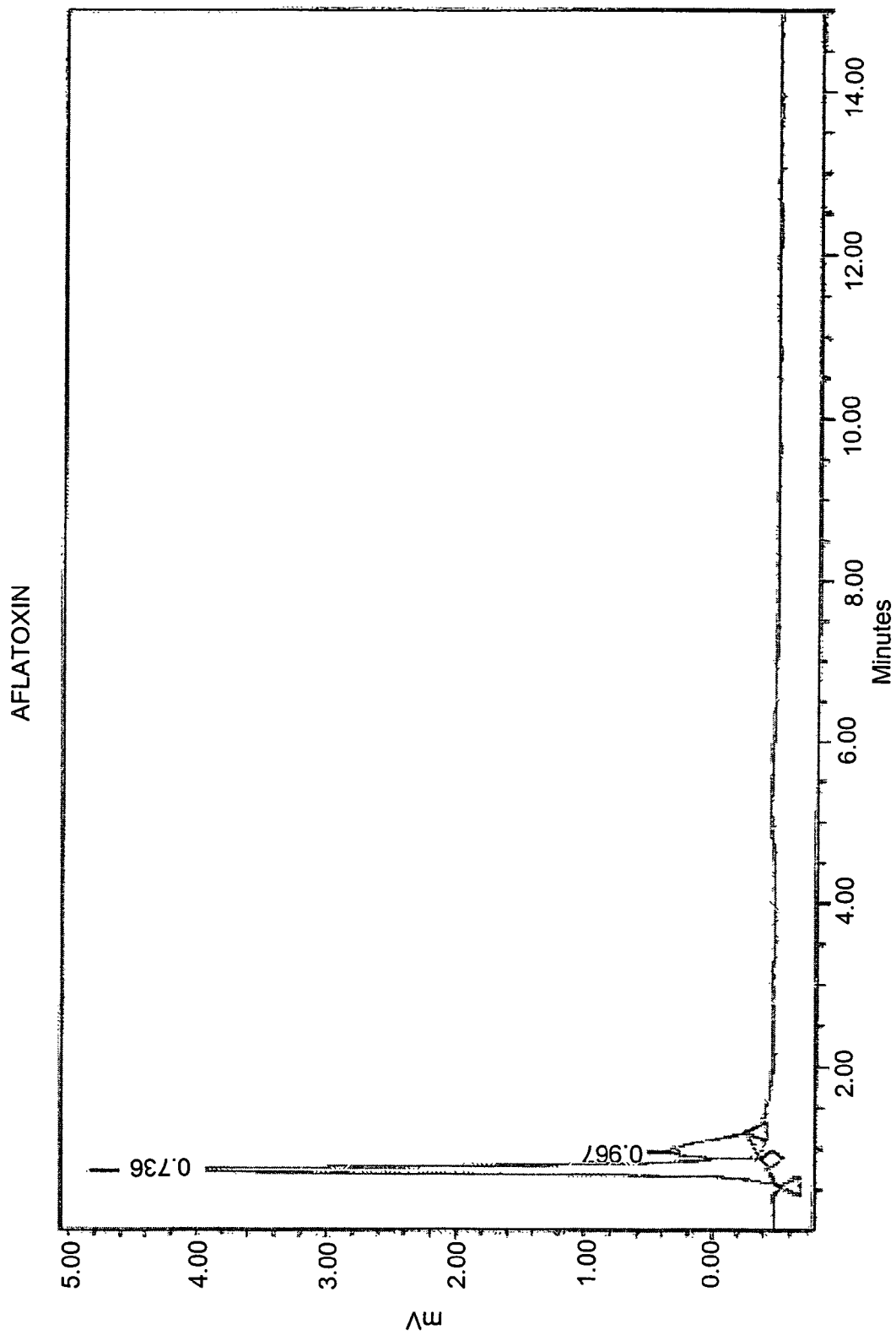

In a preliminary study, the enzyme treatment was also performed on triplicate samples containing 2.5 times higher concentration of aflatoxin than the samples reported in FIG. 7 to evaluate the efficiency of the enzyme treatment. The HPLC profile from these samples indicated complete absence of peaks associated with $AFB_1$ and $AFB_2$. (Data not shown) Thus, treatment with LOX has the ability to reduce aflatoxin to non-detectable levels. Twenty varieties of aflatoxin-contaminated corn with varying amounts of aflatoxins and lutein were analyzed in duplicate as described above for lutein and aflatoxin determination. The results of the HPLC profiles of aflatoxins indicated no detectable levels of aflatoxins in enzyme treated samples (FIG. 7), and an average lutein recovery of 0.97±0.04 mg/100 g corn (dry wt.) (Table 3).

TABLE 4

Aflatoxin Concentrations from HPLC Analysis.

| | Aflatoxin Concentration (ppb) | | | |
|---|---|---|---|---|
| Sample | $AFG_1$ | $AFB_1$ | $AFG_2$ | $AFB_2$ |
| Aflatoxins standard (100 ppb) | 36.3 | 36.4 | 9.5 | 9.6 |
| Aflatoxin-free corn | N.D. | N.D. | N.D. | N.D. |
| Aflatoxin-contaminated corn | N.D. | 4888.0 | N.D. | 368.0 |

TABLE 4-continued

Aflatoxin Concentrations from HPLC Analysis.

| Sample | Aflatoxin Concentration (ppb) | | | |
|---|---|---|---|---|
| | $AFG_1$ | $AFB_1$ | $AFG_2$ | $AFB_2$ |
| Aflatoxin-contaminated lutein extract | N.D. | 1136.0 | N.D. | 93.0 |
| Enzyme-treated lutein extract | N.D. | N.D. | N.D. | N.D. |

N.D. = Non-detected

EXAMPLE 4

Lutein Stability Following Enzyme Treatment

Figure 8:
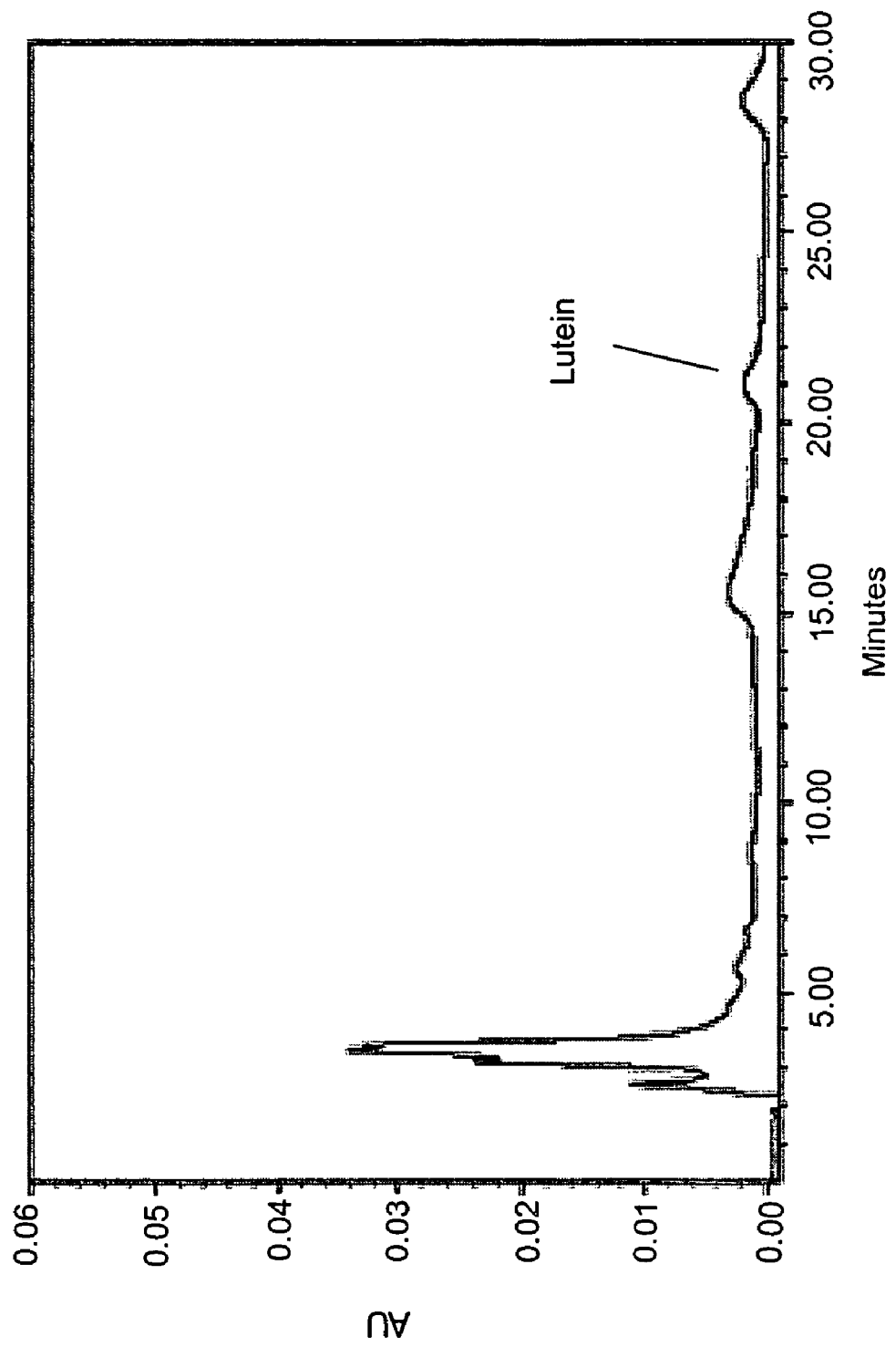

The stability of lutein was evaluated by HPLC using a $YMC_{30}$ carotenoid column after the enzyme treatment. The HPLC profile of lutein isolated from the enzyme-treated samples indicated the presence of a peak associated with lutein at ~21 min (FIG. 8). This was similar to that eluted at approximately 21.0 min in the lutein standard, as shown in FIG. 3. The small peaks that appear at retention times approximately 15.5 and 28.5 min are probably the result of lutein degradation.

Figure 9:
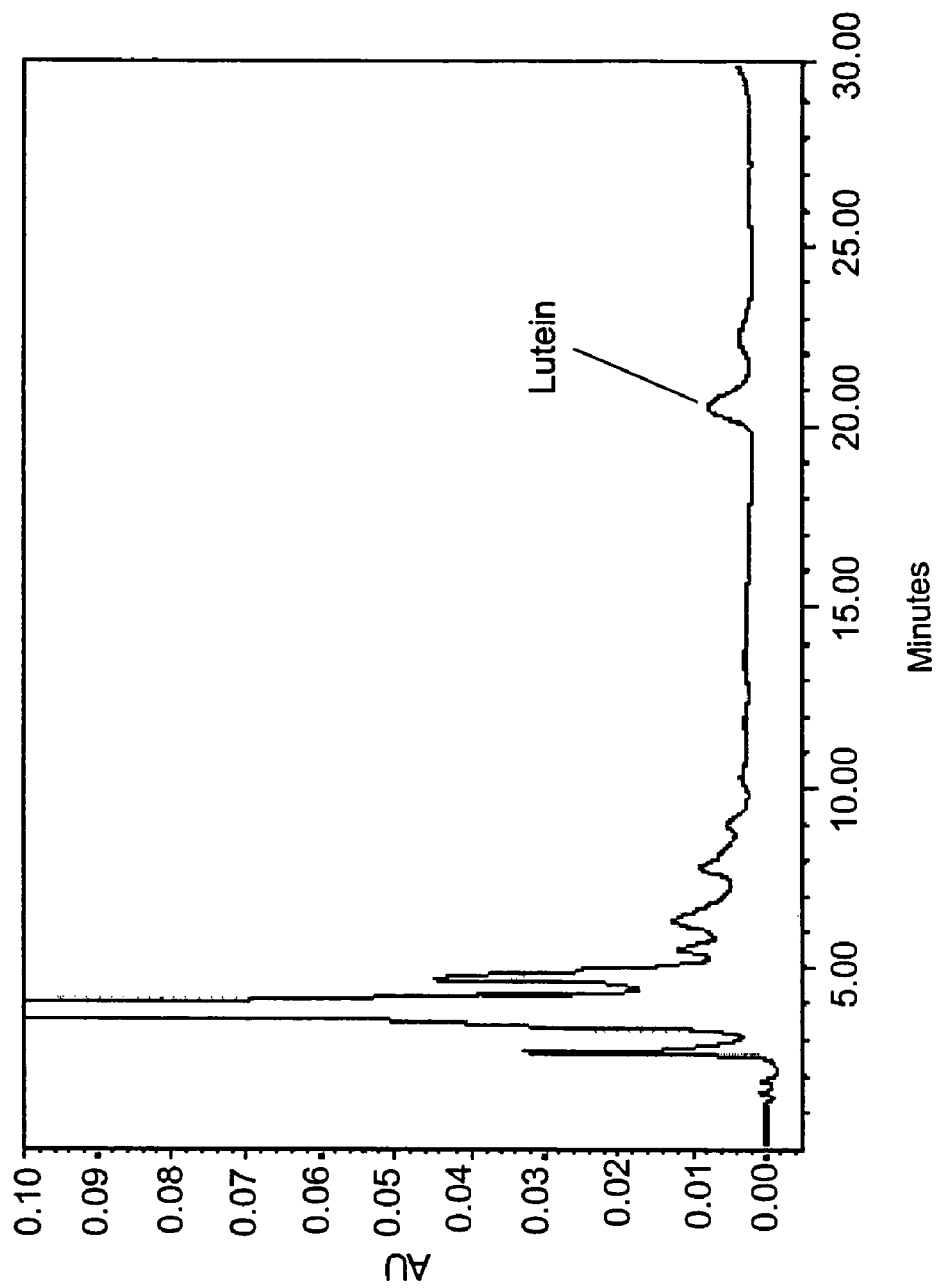

For further confirmation, the lutein samples after the enzyme treatment were spiked with different concentrations of lutein standard. The spiking procedure was performed to confirm that the peak identified at a retention time of 21.0 min was in fact lutein. As shown in FIG. 9, a single peak was identified at the same retention time as previously when spiked with a lutein standard at a concentration of 12.5 ppm. (Comparison of FIG. 9 with FIG. 3) As the lutein standard concentration was increased, the lutein peaks were more evident. Lutein peaks after spiking the enzyme-treated samples with 25 and 50 ppm lutein were similar to that above. (Data not shown) All three spiked samples were eluted at a retention time of approximately 21.0 min.

From 1.10 mg of aflatoxin-contaminated lutein from 100 g of aflatoxin-contaminated corn measured before enzyme treatment, 0.97 mg of aflatoxin-free lutein was recovered following aflatoxin displacement, a yield of 88% aflatoxin-free lutein following the enzyme treatment.

Chromatographic analysis based on the Multifunctional Column (Mycosep) method was used to determine the aflatoxin levels before and after the enzyme treatment. According to the results, the aflatoxin levels in contaminated corn were eliminated or reduced to non-detectable levels after the lipoxidase treatment. The effectiveness of the treatment was evaluated by using 20 varieties of aflatoxin-contaminated corn samples. The lipoxidase treatment was shown to be reproducible and effective. The stability of lutein following the enzyme treatment was evaluated by HPLC. Approximately 88% of the. initial lutein was. recovered after enzyme treatment.

EXAMPLE 5

An Alternate Lutein Extraction Process for Uncontaminated Corn (or other Plants)

An alternative extraction procedure was used to obtain lutein from corn samples. In this procedure, ground corn samples were turned into flakes using a Bauer flaking roll (cereal flicker). The corn flakes were then extracted with acetone at a ratio of 1:3 corn:acetone for 1 hr. using gentle shaking. The lutein-containing acetone extract was removed by filtration, and the extract set aside. A second extraction with acetone using the same procedure was then performed. The two extracts were combined, and the acetone removed by evaporation as described in Example 1, leaving a lutein-enriched oily extract. The remaining residue from the corn flakes was dried (either air dried or low temperature), and used as described below for oil and protein extraction. After the acetone removal, the lutein-rich oily extract, which contained lutein, phospholipids, and other neutral lipids, was dark red in color. This extract was stored at 4° C. overnight to separate the lutein (in an oily solution) from the phospholipids and neutral lipids that solidified and settled out. This lutein extract can be stored at −20° C. until use. Optionally, the lutein-layer was separated from the lipids/phospholipids by low speed centrifugation (approx. 4000 rpm for 20 min). The lutein yield using this technique was about 0.3% weight of original corn, and more than 90% pure. This procedure gave the best yield of lutein from corn. Additional lutein purification if necessary can be done by saponification, followed by a hexane:ether extraction as described in Example 1. Using this hexane:ether procedure, the lutein extract should be dissolved in ethanol and the solvent removed under vacuum, and these two steps repeated at least three times to remove traces of the ether:hexane mixture. The recovered lutein can then be stored at −20° C. until use.

EXAMPLE 6

Lutein Extraction from Aflatoxin-Contaminated Corn (or other Cereals)

The extraction was initially conducted as described above in Example 5 but with aflatoxin-contaminated corn. The aflatoxin followed the lutein in the extraction process. Thus, the final red extract (after removal of the acetone) of lutein, phospholipids, and neutral lipids also contained the aflatoxin. The residual "corn flakes" or meal were combined and dried, and used for oil and protein extraction as described below. As indicated below, this residual meal was shown not to be contaminated with aflatoxin by HPLC. The lutein-aflatoxin extract was further treated to separate the lutein (and aflatoxin) from the phospholipids and neutral lipids as described above for normal corn.

The lutein/aflatoxin extract was then combined with oil as described in Example 1, "Enzymatic Treatment of Extracted Lutein Residue." The extract was dissolved in the oil, then incubated with a mixture of DMSO, lipooxygenase (e.g., lipoxidase), and linoleic acid. After treatment, the lutein was removed (without the aflatoxin) with hexane:ethyl ether as described above in Example 1, "Lutein Extraction," but without a saponification step. The hexane:ethyl ether was then removed by evaporation, and pure aflatoxin-free lutein was recovered.

EXAMPLE 7

Oil Extraction from Lutein-depleted Corn Flakes

To extract the oil, the dry residual corn flakes were extracted with hexane at room temperature with shaking. The extracted oil was analyzed by HPLC and found to be free from measurable aflatoxin.

EXAMPLE 8

Protein Extraction from Lutein-depleted Corn Flakes

The residual corn flakes after oil extraction in Example 7 were dried and extracted with four-volumes of a mixture of 70% ethanol, 30% water, and 0.5 M NaCl. The extraction was conducted overnight, followed by filtration through #4 filter paper. This extract was analyzed for a protein profile by standard polyacrylamide gel electrophoresis. The extract was found to have a protein profile similar to that found in the corn flakes before the initial acetone extraction, and to be free of aflatoxin from HPLC analysis. (Data not shown).

Using the above extraction prior to the enzyme treatment, lutein has been extracted from aflatoxin-free corn with a yield of 0.3%. However, with contaminated corn, the yield was about 0.26% after enzymatic treatment.

The complete disclosures of all references cited in this application are hereby incorporated by reference. Also, incorporated by reference are the complete disclosures of the following documents: Evodokia Menelaou, "Isolation of Aflatoxin-Free Lutein from Aflatoxin-Contaminated Corn," A thesis submitted to the Department of Food Science, Louisiana State University, August, 2004, not publically accessible until Sep. 13, 2006; and S. T. Jones et al., "Storage stability of lutein during ripening of cheddar cheese," J. Dairy Sci., vol. 88, pp. 1661-1670 (2005). In the event of an otherwise irreconcilable conflict, however, the present specification shall control.

We claim:

1. A process for isolating aflatoxin-free lutein from an aflatoxin-contaminated plant source containing lutein and lipids, said method comprising the steps of:
    (a) Grinding the plant source;
    (b) Treating the ground plant source with acetone, in a concentration and for a time sufficient to extract at least some of the aflatoxin-contaminated lutein from the plant source, and then filtering the resulting mixture to separate the acetone solution with dissolved aflatoxin-contaminated lutein and lipids from undissolved plant materials;
    (c) Evaporating the filtered acetone solution for a time sufficient to concentrate the aflatoxin-contaminated lutein and lipids;
    (d) Maintaining the concentrated acetone-solution at a sufficiently low temperature and a sufficiently long time to precipitate most of the lipids from the dissolved aflatoxin-contaminated lutein;
    (e) Collecting the solution with dissolved aflatoxin-contaminated lutein;
    (f) Incubating the dissolved aflatoxin-contaminated lutein with a lipoxygenase, in a concentration and under conditions sufficient to oxidize the aflatoxin;
    (g) Saponifying the lutein with alkali;
    (h) Separating the lutein into a polar phase solvent; and
    (i) Evaporating the polar phase solvent to concentrate the lutein;

Wherein steps (a) through (i) occur consecutively in the order listed above.

2. A process as in claim 1, additionally comprising treating the lutein from step (i) with ethanol in a concentration and for a time to dissolve traces of the polar phase solvent; and evaporating the ethanol solution leaving a more highly purified lutein.

3. A process as in claim 1, wherein the plant source is selected from the group consisting of corn, cotton, peanut, soybean, rice, wheat, maize, millet, and barley.

4. A process as in claim 3, wherein the plant source comprises corn kernels.

5. A process as in claim 1, wherein a condition sufficient to oxidize the aflatoxin in step (f) is an incubation time of at least two hours.

6. A process as in claim 1, wherein a condition sufficient to oxidize the aflatoxin in step (f) is an incubation pH from about 7.0 to about 7.4.

7. A process as in claim 6, wherein the incubation pH is about 7.2.

8. A process for isolating aflatoxin-free lutein from an aflatoxin-contaminated plant source containing lutein and lipids, said method comprising the steps of:
    (a) Grinding the plant source;
    (b) Treating the ground plant source with acetone, in a concentration and for a time sufficient to extract at least some of the aflatoxin-contaminated lutein from the plant source, and then filtering the resulting mixture to separate the acetone solution with dissolved aflatoxin-contaminated lutein and lipids from undissolved plant materials;
    (c) Evaporating the filtered acetone solution for a time sufficient to concentrate the aflatoxin-contaminated lutein and lipids;
    (d) Saponifying the lipids with alkali;
    (e) Separating the aflatoxin-contaminated lutein into a polar phase solvent;
    (f) Evaporating the polar phase solvent to concentrate the aflatoxin-contaminated lutein;
    (g) Incubating the concentrated aflatoxin-contaminated lutein with a lipoxygenase, in a concentration and under conditions sufficient to oxidize the aflatoxin;
    (h) Saponifying the lutein with alkali;
    (i) Separating the lutein into a polar phase solvent; and
    (j) Evaporating the polar phase solvent to concentrate the lutein;

Wherein steps (a) through (i) occur consecutively in the order listed above.

9. A process as in claim 8, additionally comprising treating the lutein from step (i) with ethanol in a concentration and for a time to dissolve traces of the polar phase solvent; and evaporating the ethanol solution leaving a more highly purified lutein.

10. A process as in claim 8, wherein the plant source is selected from the group consisting of corn, cotton, peanut, soybean, rice, wheat, maize, millet, and barley.

11. A process as in claim 8, wherein the plant source comprises corn kernels.

12. A process as in claim 8, wherein a condition sufficient to oxidize the aflatoxin in step (g) is an incubation time of at least two hours.

13. A process as in claim 8, wherein a condition sufficient to oxidize the aflatoxin in step (g) is an incubation pH from about 7.0 to about 7.4.

14. A process as in claim 13, wherein the incubation pH is about 7.2.

* * * * *